United States Patent [19]

Hub et al.

[11] Patent Number: 5,679,876

[45] Date of Patent: Oct. 21, 1997

[54] PURIFICATION OF PENTAFLUOROETHANE

[75] Inventors: Serge Hub, Villeurbanne; Pierre Ravenel, Laval, both of France

[73] Assignee: Elf Atochem S.A., France

[21] Appl. No.: 644,053

[22] Filed: May 10, 1996

[30] Foreign Application Priority Data

May 10, 1995 [FR] France ................... 95 05519

[51] Int. Cl.$^6$ ................... C07C 17/38; C07C 17/10
[52] U.S. Cl. ................... 570/177; 570/176
[58] Field of Search ................... 570/176, 177

[56] References Cited

U.S. PATENT DOCUMENTS

| | | |
|---|---|---|
| 4,319,060 | 3/1982 | Cunningham et al. . |
| 4,873,381 | 10/1989 | Kellner et al. ................... 570/176 |
| 4,980,324 | 12/1990 | Kellner . |
| 5,057,470 | 10/1991 | Kellner . |
| 5,087,329 | 2/1992 | Felix . |

FOREIGN PATENT DOCUMENTS

| | | |
|---|---|---|
| A 0 506 525 | 3/1992 | European Pat. Off. . |
| A 0 687 660 | 9/1994 | European Pat. Off. . |
| WO 93/24224 | of 0000 | WIPO . |
| 9402439 | 2/1994 | WIPO ................... 570/177 |
| WO 94/02439 | 2/1994 | WIPO . |
| WO 94/20441 | 9/1994 | WIPO . |

*Primary Examiner*—Alan Siegel
*Attorney, Agent, or Firm*—Bell, Boyd & Lloyd

[57] ABSTRACT

The invention relates to the purification of pentafluoroethane (F125) containing chloropentafluoroethane (F115) by vapor-phase catalytic hydrogenolysis.

A catalyst based on palladium deposited on aluminium trifluoride is employed.

12 Claims, No Drawings

PURIFICATION OF PENTAFLUOROETHANE

FIELD OF THE INVENTION

The present invention relates to the field of fluorohydrocarbons and its subject is more particularly the purification of pentafluoroethane (F125 hereinafter) containing chloropentafluoroethane (F115) by vapour-phase catalytic hydrogenolysis.

BACKGROUND OF THE INVENTION

F125 is an HFC (hydrofluorocarbon) which may be employed as a substitute for F115 (a CFC, chlorofluorocarbon) in the field of low-temperature refrigeration.

Known processes for obtaining F125 include, among others, the fluorination of perchloroethylene or of its fluoro derivatives like 1,1-difluoro-1,2,2-trichloroethane (F122), 1,1-dichloro-2,2,2-trifluoroethane (F123) and 1-chloro-1,2,2,2-tetrafluoroethane (F124), the fluorination of chlorotrifluoroethylene (F1113) or the chemical reduction of F115, especially the hydrogenolysis of the latter. In most cases these routes for the synthesis of F125 produce a crude F125 which is contaminated by quantities of F115 which are not insignificant, either by formation of by-products which is due to the high temperatures needed to obtain high yields of F125 (in the case of fluorination reactions) or because of nonquantitative conversions of the starting material (in the case of the hydrogenolysis of F115).

As indicated in patent U.S. Pat. No. 5,087,329, separation of the compounds F125 and F115 by distillation is very difficult, or even impossible if it is intended to obtain a very low residual F115 content. Processes for the purification of F125 which make it possible to lower the F115 contents in the F125 produced are therefore currently being investigated.

A number of processes for the purification of F125 are already described in the prior art:

the abovementioned patent U.S. Pat. No. 5,087,329 relies on an extractive distillation consisting, before distillation, in adding to the F125-F115 mixture an extraction agent consisting of an optionally hydrogenated and/or chlorinated $C_1$-$C_4$ fluorohydrocarbon which has a boiling point of between $-39°$ C. and $+50°$ C.;

in patent application EP 508 631, which describes the production of HFC compounds by liquid phase chemical reduction of chlorine-, bromine- or iodine-containing compounds with a metal hydride or a complex of such a hydride, it is indicated that this process may be of interest for purifying some HFCs like F125;

recently, patent applications WO 94/02439 and WO 94/20441 proposed to purify F125 by hydrogenolysis of the impurities present (among others, F115) on metal catalysts deposited on carbon, alumina or fluorinated alumina.

Among the various methods of purification which are proposed, hydrogenolysis exhibits the not insignificant advantage of purifying F125 while making profitable use of the F115 impurity to be removed. However, the major disadvantage of the hydrogenolysis processes lies in the degree of stability of the catalyst activity with time. In fact, in the frequently severe reaction conditions which are necessary for converting the reactants, the catalyst becomes deactivated with time; it must then be replaced at regular intervals with a fresh charge, or an efficient means of regenerating the spent catalyst must be found.

With this in mind, a number of techniques for regeneration of hydrogenolysis catalysts are to be found described in the literature. Patent application WO 93/24224 proposes the oxidation of the spent catalyst with oxygen or an oxidizing agent. Treatments with chlorine (patent U.S. Pat. No. 5,057,470) or with CFC, which may be the reactant to be converted (patent U.S. Pat. No. 4,980,324) are also found to be effective. However, these processes merely reactivate the catalysts, which still exhibit the same disadvantages after the treatment.

DESCRIPTION OF THE INVENTION

It has now been found that, in contrast to the other catalysts commonly employed: Pd/C, Pd/$Al_2O_3$ or Pd/fluorinated alumina, a catalyst based on palladium deposited on aluminium trifluoride ($AlF_3$) has the property of being stable in the reaction of purification of F125 from the F115 impurity by hydrogenolysis.

The subject of the invention is therefore a process for the purification of a pentafluoroethane (F125) containing chloropentafluoroethane (F115), by vapor-phase catalytic hydrogenolysis, characterized in that a catalyst based on palladium deposited on aluminium trifluoride is employed.

Aluminium trifluoride is a commercially available support whose BET surface is generally greater than 70 $m^2$/g. According to the invention it is employed advantageously in the form of tablets, but it would not constitute a departure from the scope of the present invention to employ other forms such as beads, extrudates, etc.

The catalyst employed according to the invention can be prepared in accordance with the conventional techniques for impregnating the support with an aqueous or organic solution of a palladium derivative, in a quantity which is sufficient for the palladium weight content of the catalyst to be between 0.1 and 10%, preferably between 0.5 and 5%. After impregnation the water or the organic solvent is removed by evaporation and the solid obtained is subjected to a heat treatment at a temperature ranging from 100° to 500° C. (preferably 200° to 350° C.) and under a hydrogen and/or nitrogen stream (preferably at a pressure of 1 to 5 bars) to liberate the palladium. The nature of the palladium derivative is of no importance and may be, for example, the chloride, acetate, acetylacetonate, nitrate or the organometallic compounds of the chloride. The solvent may be water or an organic compound. Organic solvents which may be employed are chlorine-containing methane or ethane derivatives (for example chloroform, methylene chloride and carbon tetrachloride), aromatic solvents (for example benzene, toluene and chlorobenzene) or amines or alkanolamines (for example pyridine and ethanolamine).

The temperature of the purification treatment is generally between 200° and 450° C., but it is preferable to work between 250° and 350° C. The treatment may be performed at a pressure of between 1 and 50 bars; an increase in pressure increases the contact time and makes it possible to attain higher conversions at a given temperature.

Although the process according to the invention may be applied to mixtures containing high F115 contents, it is more particularly intended for the treatment of a crude F125 in which the molar content of F115 does not exceed 10%. The hydrogen is employed in a quantity such as to make the $H_2$/F115 molar ratio between 1 and 40, preferably between 2 and 10.

The total hourly flow rate of gas ($H_2$+F125+F115) may range from 0.01 to 20 moles per liter of catalyst and is preferably between 0.5 and 15 moles.

The following examples illustrate the invention without limiting it.

EXAMPLE 1

Comparative 50 ml of a commercial Pd/Al$_2$O$_3$ catalyst containing 2% by weight of palladium were introduced into an electrically heated Inconel tubular reactor 45 cm in length and 2.72 cm. in internal diameter. A mixture of hydrogen, pentafluoroethane (F125) and chloropentafluoroethane (F115) was passed over the catalyst in the following operating conditions:

| Temperature | 280° C. |
|---|---|
| Hydrogen flow rate | 0.016 moles/hour |
| F125 flow rate | 0.244 moles/hour |
| F115 flow rate | 0.008 moles/hour |

Analysis, carried out by in-line chromatography (VPC) at the reactor exit, gave the following results:

| TIME (hours) | F115 CONVERSION (%) | SELECTIVITY FOR F125 (%) |
|---|---|---|
| 25 | 99.0 | 98.7 |
| 30 | 98.9 | 98.8 |
| 50 | 98.7 | 98.9 |
| 60 | 98.8 | 98.7 |
| 100 | 98.3 | 98.7 |
| 120 | 97.9 | 98.8 |
| 140 | 95.2 | 98.9 |
| 150 | 95.0 | 98.7 |
| 210 | 90.0 | 98.8 |
| 260 | 84.5 | 98.9 |

The activity of the catalyst is not stable with time: it drops by approximately 15% after 260 hours' continuous treatment.

EXAMPLE 2

Comparative a) Preparation of the catalyst
(Pd/fluorinated alumina)

75 ml (50 g) of a commercial alumina (180 m$^2$/g) in the form of beads (2 mm in diameter) were charged into a tubular reactor and were dried for 18 hours at 180° C. under a stream of air (1 mole/hour). The temperature was then raised from 180° C. to 300° C. over 5 hours with a mixture of air and hydrofluoric acid (2 moles/hour and 0.8 moles/hour respectively), and then a treatment at 400° C. under pure HF (0.8 moles/hour) was carried out for 8 hours. A fluorinated alumina was then obtained containing 64.5 mass % of fluorine and with a BET surface of 20 m$^2$/g.

50 ml (28 g) of the fluorinated alumina prepared in the manner described above were charged into a rotary evaporator. After degassing for 3 hours at 100° C. under reduced pressure (1 kPa), 50 ml of a solution of palladium acetate in toluene containing 0.6 g of palladium were introduced and then the solvent was evaporated off at reduced pressure (26 kPa) and the residue was dried at 80° C. It was then treated at 250° C. for 2 hours under a stream of nitrogen (5 Sl/h) and a Pd/fluorinated alumina catalyst containing 2.3% of palladium was thus obtained.

b) Purification of F125

50 ml of the catalyst whose preparation is described above were introduced into an electrically heated Inconel tubular reactor 45 cm in length and 2.72 cm in internal diameter and then a mixture of hydrogen, pentafluoroethane (F125) and chloropentafluoroethane (F115) was passed over the catalyst in the following operating conditions:

| Temperature: | 270° C. |
|---|---|
| Hydrogen flow rate | 0.018 moles/hour |
| F125 flow rate | 0.271 moles/hour |
| F115 flow rate | 0.009 moles/hour |

The analysis, performed by in-line chromatography (VPC) at the reactor exit, gave the following results:

| TIME (hours) | F115 CONVERSION (%) | SELECTIVITY FOR F125 (%) |
|---|---|---|
| 10 | 70.4 | 97.9 |
| 20 | 60.8 | 97.7 |
| 25 | 53.9 | 97.1 |
| 30 | 48.3 | 96.9 |
| 40 | 32.7 | 96.2 |
| 50 | 22.8 | 94.4 |
| 60 | 17.3 | 91.9 |
| 70 | 14.7 | 91.0 |
| 90 | 13.1 | 90.5 |

The activity of the catalyst is not stable with time.

EXAMPLE 3 a) Preparation of the catalyst (Pd/aluminium trifluoride)

50 ml (36 g) of commercial aluminium fluoride with a BET surface of 110 m$^2$/g, preformed into tablets (5 mm in diameter by 3 mm in height) were charged into a rotary evaporator. After degassing for 3 hours at 100° C. under reduced pressure (1 kPa), 50 ml of a solution of palladium acetate in toluene containing 1 g of palladium were introduced and then the solvent was evaporated off at reduced pressure (26 kPa) and the residue was dried at 80° C. It was then treated at 250° C. for 2 hours under a stream of nitrogen (5 Sl/h) and a Pd/aluminium trifluoride catalyst containing 2.4% of palladium was thus obtained.

b) Purification of F125

43 ml of the catalyst whose preparation is described above were introduced into an electrically heated Inconel tubular reactor 45 cm in length and 2.72 cm in internal diameter and then a mixture of hydrogen, pentafluoroethane (F125) and chloropentafluoroethane (F115) was passed over the catalyst in the following operating conditions:

| Temperature: | 290° C. |
|---|---|
| Hydrogen flow rate | 0.018 moles/hour |
| F125 flow rate | 0.225 moles/hour |
| F115 flow rate | 0.009 moles/hour |

The analysis, performed by in-line chromatography (VPC) at the reactor exit, gave the following results:

| TIME (hours) | F115 CONVERSION (%) | SELECTIVITY FOR F125 (%) |
|---|---|---|
| 10 | 98.5 | 98.4 |
| 50 | 98.8 | 98.3 |
| 70 | 98.5 | 98.5 |
| 140 | 98.6 | 98.6 |
| 150 | 98.7 | 98.8 |
| 160 | 98.8 | 98.9 |
| 180 | 98.6 | 98.8 |
| 230 | 98.6 | 98.7 |

-continued

| TIME (hours) | F115 CONVERSION (%) | SELECTIVITY FOR F125 (%) |
| --- | --- | --- |
| 250 | 98.6 | 98.9 |
| 320 | 98.6 | 99.0 |
| 350 | 98.5 | 98.8 |
| 400 | 98.6 | 98.9 |

The catalyst is perfectly stable.

We claim:

1. Process comprising the purification of a crude pentafluoroethane containing chloropentafluoroethane by vapor phase catalytic hydrogenolysis, by employing a catalyst based on palladium deposited on a support consisting of aluminium trifluoride.

2. Process according to claim 1, wherein the aluminium trifluoride has a BET surface greater than 70 m$^2$/g.

3. Process according to claim 1 wherein the palladium weight content of the catalyst is between 0.1 and 10%.

4. Process according to claim 1 wherein the operation is carried out at a temperature of between 200° and 450° C., between.

5. Process according to claim 1 wherein the operation is carried out at a pressure of between 1 and 50 bars.

6. Process according to claim 1 wherein the hydrogen/chloropentafluoroethane molar ratio is between 1 and 40.

7. Process according to claim 1 wherein the total flow rate of gas per liter of catalyst is between 0.01 and 20 moles.

8. Process according to claim 1 wherein the molar content of chloropentafluoroethane in the crude pentafluoroethane to be treated does not exceed 10%.

9. Process according to claim 3, wherein the weight content is between 0.5 and 5%.

10. Process according to claim 4, wherein the temperature is between 250° and 350° C.

11. Process according to claim 6, wherein the molar ratio is between 2 and 10.

12. Process according to claim 7, wherein the total flow rate is between 0.5 and 15 moles.

* * * * *